(12) United States Patent
Ferguson, Jnr. et al.

(10) Patent No.: US 9,885,566 B2
(45) Date of Patent: Feb. 6, 2018

(54) APPARATUS FOR DETERMINING THICKNESS OF LINING LAYER

(71) Applicant: JOHNSON MATTHEY PUBLIC LIMITED COMPANY, London (GB)

(72) Inventors: Dave Doyle Ferguson, Jnr., Cleveland (GB); Emanuele Ronchi, Cleveland (GB); Carl Robert Tipton, North Yorkshire (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/324,170

(22) PCT Filed: Jul. 23, 2015

(86) PCT No.: PCT/GB2015/052138
§ 371 (c)(1),
(2) Date: Jan. 5, 2017

(87) PCT Pub. No.: WO2016/012799
PCT Pub. Date: Jan. 28, 2016

(65) Prior Publication Data
US 2017/0199032 A1    Jul. 13, 2017

(30) Foreign Application Priority Data

Jul. 24, 2014 (GB) .................. 1413119.7
Feb. 2, 2015 (GB) .................. 1501679.3

(51) Int. Cl.
*G01B 15/02* (2006.01)
*G01N 23/203* (2006.01)

(52) U.S. Cl.
CPC .......... *G01B 15/02* (2013.01); *G01N 23/203* (2013.01); *G01N 2223/1013* (2013.01); *G01N 2223/61* (2013.01); *G01N 2223/633* (2013.01)

(58) Field of Classification Search
CPC .......... G01B 15/02; G01B 2223/1013; G01B 2223/61; G01B 2223/633; G01B 23/203;
(Continued)

(56) References Cited

U.S. PATENT DOCUMENTS 3,315,076 A   4/1967   Jordan
3,353,023 A   11/1967  Lowery et al.
(Continued)

FOREIGN PATENT DOCUMENTS

CA   902271   6/1972
CA   1312967  1/1993
(Continued)

OTHER PUBLICATIONS

United Kingdom Search Report dated Dec. 8, 2014; Application No. GB1413119.7.

*Primary Examiner* — Mark R Gaworecki
(74) *Attorney, Agent, or Firm* — Baker & Hostetler LLP

(57) ABSTRACT

An apparatus (2) for determining thickness of refractory material (4) lining a metal vessel (6) is disclosed. The apparatus includes a radiation source (16) for emitting radiation through a metal wall of the vessel and into the refractory material, wherein some of the radiation is scattered by the refractory material, and a radiation detector (20) for detecting radiation scattered by the refractory material through the wall of the vessel. A converter provides an output signal dependent on the quantity of radiation scattered by the refractory material through the wall of the vessel and detected by the radiation detector.

16 Claims, 6 Drawing Sheets

(58) Field of Classification Search
CPC ....... G01N 2223/1013; G01N 2223/61; G01N 2223/633; G01N 23/203
See application file for complete search history.

(56) References Cited

U.S. PATENT DOCUMENTS

| | | | |
|---|---|---|---|
| 3,412,328 A | 11/1968 | Lowery | |
| 3,492,479 A | 1/1970 | Lowery et al. | |
| 3,544,793 A | 12/1970 | Bless et al. | |
| 3,854,042 A | 12/1974 | Ott | |
| 4,581,599 A | 4/1986 | Toms, II | |
| 4,641,030 A | 2/1987 | Regimand | |
| 4,701,868 A | 10/1987 | Regimand | |
| 4,749,858 A | 6/1988 | Young | |
| 4,766,319 A | 8/1988 | Regimand | |
| 4,791,656 A | 12/1988 | Pratt, Jr. et al. | |
| 4,874,950 A | 10/1989 | Regimand | |
| 4,918,712 A | 4/1990 | Le Floc'h et al. | |
| 4,947,045 A | 8/1990 | Birks et al. | |
| 5,195,117 A | 3/1993 | Ong | |
| 5,442,186 A | 8/1995 | Walker et al. | |
| 5,666,394 A | 9/1997 | Swanson | |
| 5,821,862 A | 10/1998 | MacKenzie | |
| 6,238,522 B1 | 5/2001 | Graf | |
| 8,692,184 B1 | 4/2014 | Troxler et al. | |
| 8,767,912 B1 | 7/2014 | Alzaidi | |
| 2001/0055363 A1 | 12/2001 | Troxler et al. | |
| 2007/0046289 A1 | 3/2007 | Troxler | |
| 2009/0237678 A1 | 9/2009 | Brzoska et al. | |
| 2010/0198542 A1 | 8/2010 | Troxler | |
| 2011/0035182 A1 | 2/2011 | Troxler | |
| 2011/0194672 A1 | 8/2011 | Troxler | |
| 2012/0085899 A1 | 4/2012 | Troxler et al. | |
| 2013/0026354 A1 | 1/2013 | Troxler | |

FOREIGN PATENT DOCUMENTS

| | | |
|---|---|---|
| CA | 2296634 | 7/2000 |
| CN | 1036451 | 10/1989 |
| CN | 2490578 | 5/2002 |
| CN | 203161209 | 8/2013 |
| EP | 0072367 | 2/1983 |
| EP | 120676 | 10/1984 |
| EP | 246937 | 11/1987 |
| EP | 501847 | 9/1992 |
| EP | 545784 | 6/1993 |
| EP | 630476 | 12/1994 |
| EP | 955518 | 11/1999 |
| EP | 1303752 | 4/2003 |
| EP | 1327878 | 7/2003 |
| EP | 1357382 | 10/2003 |
| EP | 1636543 | 3/2006 |
| EP | 1166095 | 8/2007 |
| EP | 1932020 | 6/2008 |
| EP | 2042859 | 4/2009 |
| EP | 2238600 | 10/2010 |
| FR | 2026501 | 9/1970 |
| FR | 2343996 | 10/1977 |
| GB | 1038112 | 8/1966 |
| GB | 2336903 | 11/1999 |
| GB | 2411717 | 9/2005 |
| JP | 58223006 | 12/1983 |
| JP | 59107204 | 6/1984 |
| JP | 60021405 | 2/1985 |
| JP | 63171308 | 7/1988 |
| JP | 08261741 | 10/1996 |
| JP | 2003240528 | 8/2003 |
| JP | 2007121202 | 5/2007 |
| JP | 2007121203 | 5/2007 |
| JP | 2008145141 | 6/2008 |
| JP | 2009258115 | 11/2009 |
| JP | 2011237327 | 11/2011 |
| KR | 9004689 | 7/1990 |
| WO | 9322661 | 11/1993 |
| WO | 9612175 | 4/1996 |
| WO | 9914581 | 3/1999 |
| WO | 200157505 | 8/2001 |
| WO | 0203055 | 1/2002 |
| WO | 2004113834 | 12/2004 |
| WO | 2005088245 | 9/2005 |
| WO | 2007120179 | 10/2007 |
| WO | 2009089172 | 7/2009 |
| WO | 2009121916 | 10/2009 |
| WO | 2012170580 | 12/2012 |

APPARATUS FOR DETERMINING THICKNESS OF LINING LAYER

The present invention relates to an apparatus for determining thickness of a lining layer of a metal vessel, and relates particularly, but not exclusively, to an apparatus for determining thickness of a refractory lining layer of a steel walled fluid catalytic cracking unit.

Fluid catalytic cracking units used for cracking of hydrocarbons in an oil refinery typically utilize steel vessels lined with refractory material 100 to 125 mm in thickness. These units are generally designed to run continuously for about 5 years containing a reaction at an operating temperature of about 500 degrees C., and the refractory material provides thermal insulation to the steel wall of the vessel to keep the temperature of the steel wall at about 100 to 300 degrees C., while also providing the steel wall with erosion protection from the catalyst. Typically, a thickness of about 1 inch of refractory material will sufficiently protect the steel wall, and if the thickness of the refractory material becomes less than about 25 mm, hot spots will occur on the steel wall.

It is known to carry out a thermographic inspection of the exterior of the steel wall during operation of the unit to detect hotspots in the steel wall which generally indicate regions of less than 25 mm thickness of refractory material, thereby indicating that the refractory material needs to be replaced. However, it has not hitherto been possible to determine the remaining thickness of refractory material, during operation of the unit, when more than 25 mm thickness of refractory remains, as a result of which it becomes necessary to shut down the fluid catalytic cracking unit at very significant cost to carry out measurement of the remaining thickness of and any necessary replacement of refractory material.

Preferred embodiments of the present invention seek to overcome the above disadvantage of the prior art.

According to the present invention, there is provided an apparatus for determining thickness of material lining a metal vessel, the apparatus comprising:

radiation emitting means for emitting radiation through a metal wall of the vessel and into said lining material, wherein some of said radiation is scattered by said lining material;

radiation detecting means for detecting radiation scattered by said lining material through the wall of the vessel; and output means for providing at least one output signal dependent on the quantity of radiation scattered by said lining material through the wall of the vessel and detected by said radiation detecting means.

By providing radiation emitting means for emitting radiation through a metal wall of the vessel and into the lining material, wherein some of said radiation is scattered by the lining material, and radiation detecting means for detecting radiation scattered by the lining material through the wall of the vessel, this provides the advantage of enabling the thickness of remaining lining material lining the vessel to be determined while the vessel is in operation. This enables the significant cost of shutting down the vessel in the case of fluid catalytic cracking units or refractory lined furnaces to be avoided.

The radiation emitting means may be adapted to emit gamma radiation.

The radiation detecting means may be adapted to detect gamma radiation.

The radiation detecting means may comprise at least one scintillation crystal and at least one photomultiplier.

The apparatus may further comprise first adjustment means for adjusting a distance between the radiation emitting means and the radiation detecting means.

This provides the advantage of enabling the output signal to be matched to the thickness range of lining material of interest.

The apparatus may further comprise second adjustment means for adjusting a distance of the radiation emitting means and/or radiation detecting means from the wall of the vessel.

This provides the advantage of enabling the output signal to be matched to the thickness range of lining material of interest.

The apparatus may further comprise shielding means for attenuating radiation transmitted directly from said radiation emitting means to said radiating detection means.

This provides the advantage of enabling radiation backscattered by the lining material to be more easily detected.

The shielding means may comprise a collimator member of radiation attenuating material having at least one slot for accommodating said radiation emitting means. The radiation emitting means may be arranged between 5 mm and 40 mm from an edge of said slot in a first direction.

At least one said slot may extend 10 mm to 50 mm from said radiation emitting means in a second direction.

The apparatus may further comprise attraction means for maintaining the radiation emitting means and/or radiation detecting means within a predetermined distance of the wall of the vessel.

This provides the advantage of keeping the distance of the radiation emitting means and radiation detection means from the wall constant, thereby ensuring consistency of results obtained from a scan of the wall.

The attraction means may comprise at least one magnet.

The attraction means may comprise at least one magnetic wheel adapted to engage a wall of the vessel.

The apparatus may further comprise scanning means for enabling the apparatus to scan a surface of the vessel assisted by gravity.

The scanning means may comprise at least one winch apparatus.

The lining material may comprise more than one material. In such a case the materials may be present as layers. One such material may be present in the form of a deposit or accretion of or formed from the contents of the vessel over a period of time. Such deposits are often deleterious to the functioning of the vessel so their presence and amount may be required to be monitored. The lining material may further comprise deposits of a different material on a surface thereof. As an example, the lining material may comprise a refractory material on which is deposited a carbon material. Such carbon material may be a product of a process which is carried out within the vessel. The lining material may comprise a refractory material, a glass, a mineral material, a metal, a polymeric material a scale or other material. The lining material may comprise refractory material.

The apparatus may comprise an air gap located such that, during operation of the apparatus, the air gap is between the detecting means and the surface of the object being scanned. The apparatus may further comprise air extraction means operable to vent air from the air gap out of the apparatus. The air extraction means may comprise a fan. The apparatus may comprise ducting linking the air extraction means to the air gap. The provision of an air gap and means to circulate air out of the air gap may be advantageous when scanning objects, such as fluid catalytic cracking units, with a high surface temperature. In such operations, the detecting means may become overheated during extended use. In order to reduce or eliminate the need for pauses in the operation to allow the detector to cool, it is desirable to prevent the temperature of the detecting means rising too quickly. The invention advantageously achieves that by maintaining a curtain of air between the detecting means and the surface of the vessel. By providing air extraction means to vent air from the air gap, thus causing new ambient air to be drawn in to replace the extracted air, the invention prevents the temperature of the air in the air curtain rising and heating the detecting means.

Most preferably, the apparatus comprises air supply means configured to draw ambient air from the apparatus' surroundings and urge the ambient air towards the air gap. In that way a circulation of ambient air may be created in the region of the entrance to the air gap. Thus the air drawn into the air gap as a result of the action of the extraction means may be closer to the ambient air temperature. The air supply means may comprise a fan. The apparatus may be configured such that, in operation, a greater volume of air is urged toward the air gap by the air supply means than is drawn into the air gap by the action of the air extraction means. The excess air may be vented from the apparatus, for example from the sides or end of the apparatus, thus preventing a build-up of hot air at the entrance to the air gap (which in operation may be in close proximity to the hot object being scanned). In some embodiments the ambient air may be urged around the detecting means and into a central region of the air gap. For example, the ambient air may flow around the detecting means and into the central region of the air gap. The air flow may then flow away through the air gap, for example by flowing outwardly from the central region of the air gap through peripheral regions of air gap. Thus in such embodiments a flow of ambient air past the detector and through the air gap may be established. The flow may be established by air supply means, such as a fan, urging the air flow past the detector and through the air gap, or it may be established by air extraction means, such as a fan, drawing the air past the detector and through the air gap.

Preferably the apparatus comprises a sheet of material, such as a faceplate, located such that, during operation of the apparatus, the sheet is between the detecting means and the surface of the object being scanned. Preferably the sheet is between the air gap and the surface of the object being scanned. Preferably the sheet at least partially defines the air gap, for example the sheet may define a side of the air gap. Most preferably the detection means and/or the shielding means define an opposite side of the air gap, such that the air gap is located between the sheet and the detecting means and/or the shielding means. Air may pass across the front of the detecting means from one side of the air gap to another or it may flow past the detecting means into a central region of the air gap and then away through all sides of the air gap. That may advantageously provide a well-defined air path across the front of the detecting means, or past the detecting means, so as to restrict the heat reaching the detecting means. Preferably the surface of the sheet nearest the object being scanned during operation of the apparatus is at least partially reflective. For example, the surface may be a polished metal surface, for example a polished steel surface. That may advantageously aid in reflecting heat away from the detecting means.

According to a second aspect of the invention there is provided a method of determining thickness of lining material lining a metal vessel, the method comprising:

emitting radiation from radiation emitting means through a metal wall of the vessel and into said lining material, wherein some of said radiation is scattered by said lining material;

detecting, using radiation detecting means, radiation scattered by said lining material through the wall of the vessel; and providing at least one output signal dependent on the quantity of radiation detected.

The method may comprise maintaining an air curtain, that is, a curtain of flowing air, between the radiation detecting means and the wall of the vessel. For example, the air curtain may be formed in an air gap located between the radiation detecting means and the wall. It will be understood that other parts of the apparatus, for example the collimator, may be at least partially between the radiation detecting means and the wall and that the air gap may be located, for example, between the collimator and a faceplate of the apparatus. In that way the air gap is located between the detecting means and the wall. The air curtain may flow across the air gap or the air curtain may flow past the detector to a central region of the air gap and then flow away through the air gap. In some embodiments, the air curtain flows in substantially one direction along the faceplate of the apparatus. In some embodiments the air curtain flows past the detector and towards the faceplate of the apparatus, and then deflects along the faceplate to flow away through the air gap. The air curtain may exit the air gap in multiple directions through multiple exits.

Preferably the method comprises withdrawing air from an air gap located between the radiation detecting means and the wall of the vessel. Most preferably, the method further comprises urging air, for example ambient air from the surroundings, toward an entrance of the air gap using air supply means. The air supply means may, for example, be a fan. Preferably a greater volume of air is urged toward the air gap by the air supply means than is withdrawn from the air gap. Withdrawing air from the air gap will cause air to be drawn into the air gap.

However, urging an excess of air toward the entrance of the air gap such that at least some of the urged air is not drawn into the air gap and is instead vented away from the entrance of the air gap, for example through the sides or end of the apparatus, may assist in maintaining a fresh supply of ambient air (that being air taken from the surroundings of the apparatus) and preventing the build-up of a region of air, at the entrance to the air gap, that is already heated by its proximity to the wall. The air supply means may also direct air across at least one surface of the detecting means or its surroundings (for example, a collimator surrounding the detecting means), which may advantageously remove heat from the detecting means and help prevent the temperature of the detecting means from rising too quickly. The surface may, for example, be a rear surface in that it is a surface on the opposite side of the detecting means to the wall. In some embodiments the air supply may direct air to a central region of the air gap via a path across at least one surface of the detecting means. The air may then flow away from the central region and exit the air gap through the peripheral regions of the air gap.

It will be appreciated that features described in relation to one aspect of the invention may be equally applicable to other aspects of the invention. For example features of the apparatus of the invention may be applied to the method of the invention and vice versa. Also features may not be part of, and may be excluded from, particular aspects of the invention.

A preferred embodiment of the invention will now be described, by way of example only, and not in any limitative sense, with reference to the accompanying drawings in which.

Figure 1:
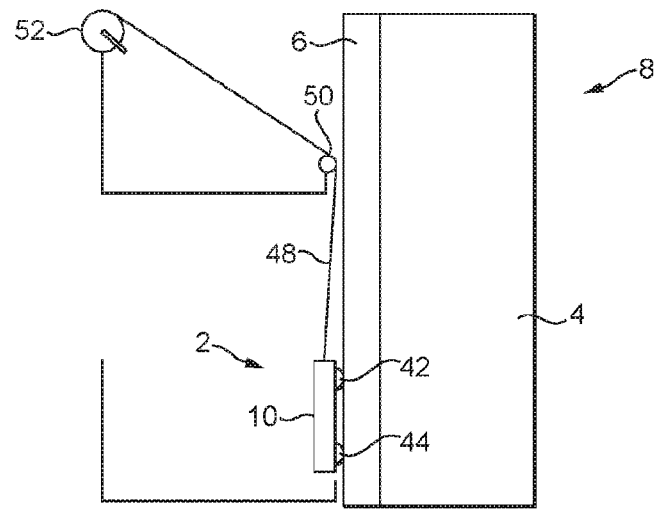
FIG. 1 is a schematic view of a thickness measuring apparatus embodying the present invention scanning a refractory lined metal vessel.
Figure 5:
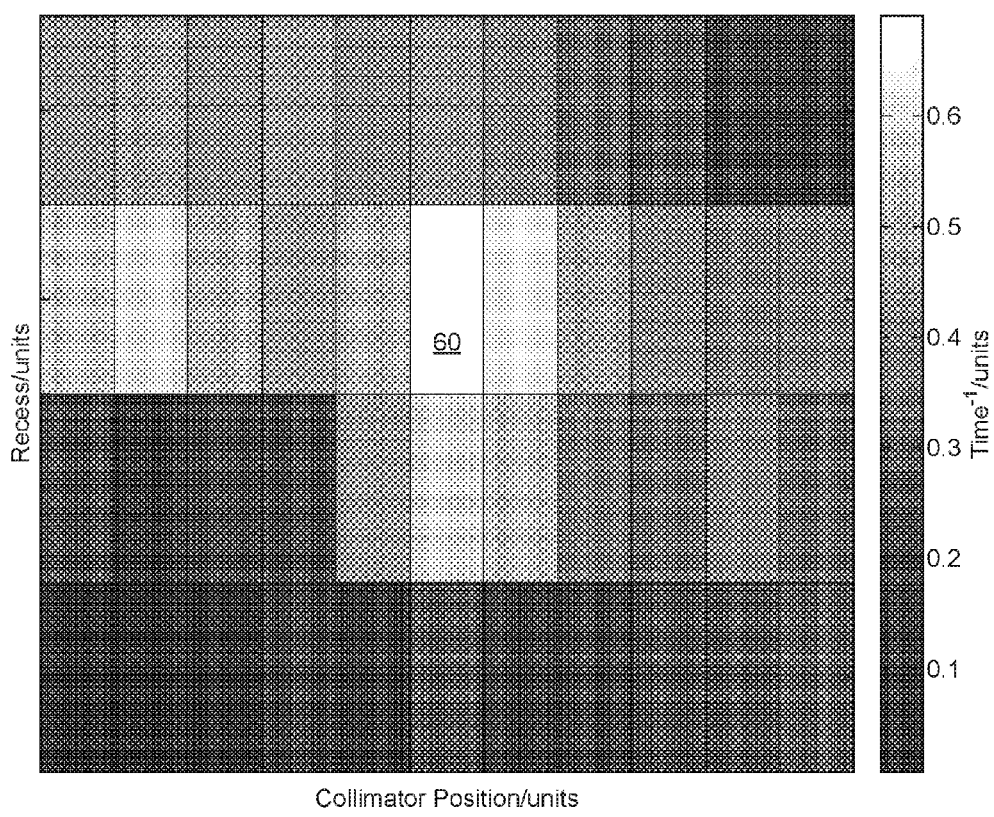
Figure 6:
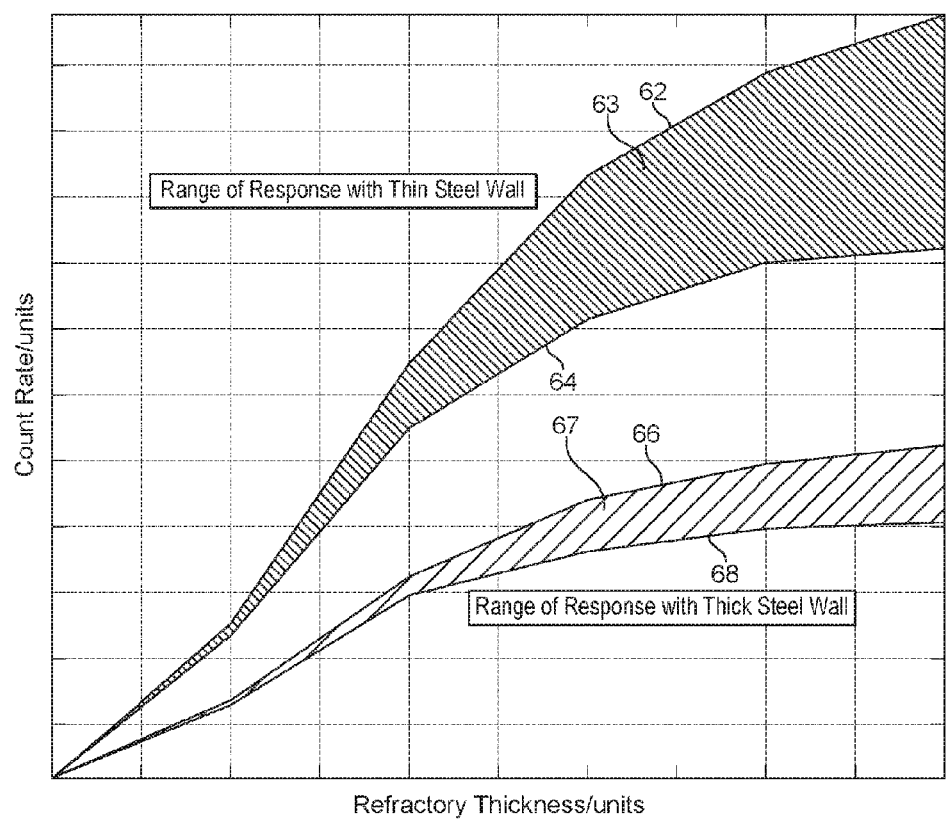
Figure 7:
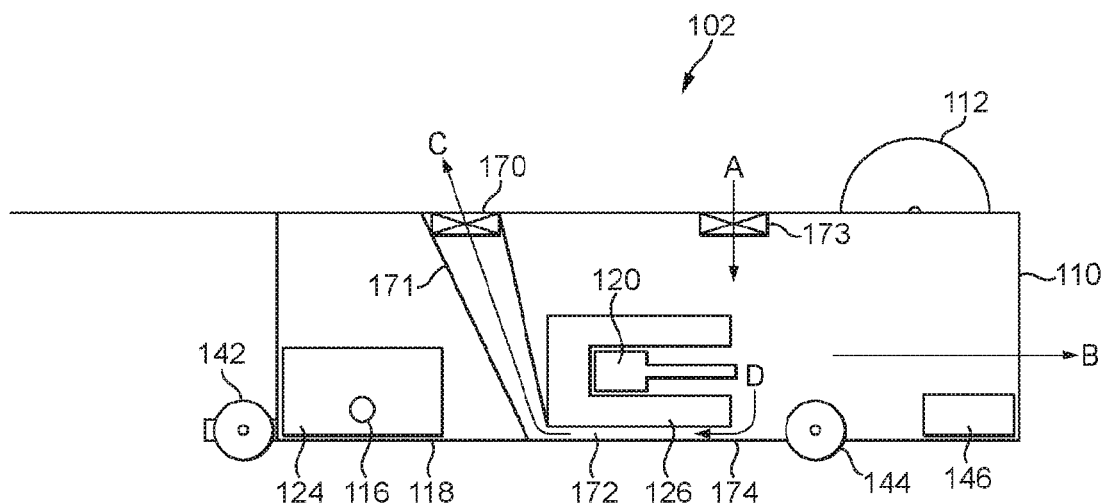

FIG. 5 indicates predicted response speed of a detector of the apparatus of FIG. 1;

FIG. 6 is a graph showing predicted variation of counter rates with thickness of refractory material for different steel wall thicknesses for the apparatus of FIG. 1; and FIG. 7 is a thickness measuring apparatus embodying a further embodiment of the invention.

Figure 2:
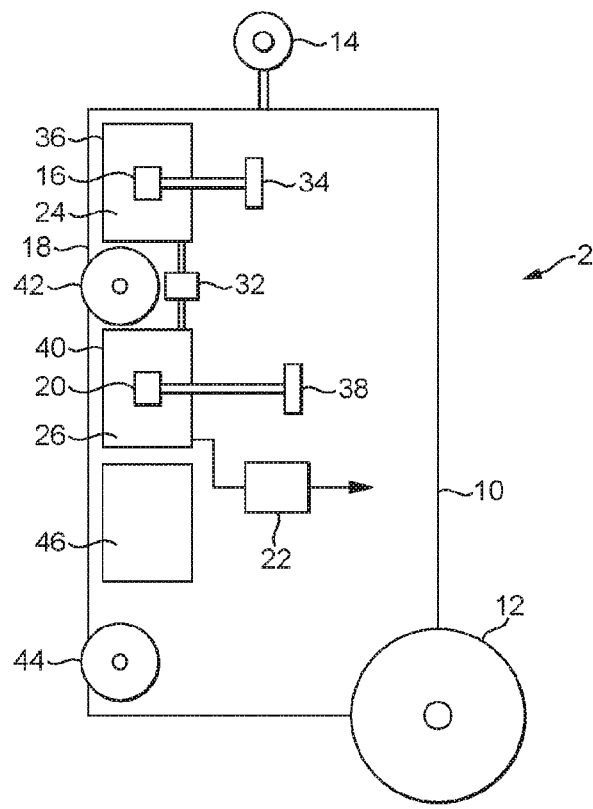
FIG. 2 is a schematic cross sectional view of part of the apparatus of FIG. 1.

Referring to FIGS. 1 and 2, an apparatus 2 for measuring thickness of refractory material 4 lining a metal wall 6 of a vessel such as a steel walled fluid catalytic cracking unit 8 has a body 10 having transport wheels 12 adjacent one end thereof and a lifting eye bolt 14 arranged adjacent the other end thereof. Radiation emitting means in the form of a 740 MBeq Cs-137 source 16 of gamma radiation is arranged adjacent one face 18 of the body 10 and radiation detecting means in the form of a 50 mm cylindrical sodium iodide crystal gamma radiation detector 20 is arranged on the same face 18 of the body 10 so that the crystal axis of the detector 20 can be arranged generally parallel to the wall 6 of the unit 8. The detector 20 is connected to output means in the form of a suitable converter 22 for outputting a signal representing the number of counts by the detector 20.

Shielding means in the form of a first collimator 24 around the source 16 and a second collimator 26 around the detector 20 minimise the number of gamma photons passing directly from the source 16 to the detector 20. The first collimator 24 comprises lead shielding having slots generally in the plane of FIG. 2 to cause a beam 28 of radiation (FIG. 3) to be directed through the wall 6 and into the refractory material 4. It is found that particularly advantageous results are achieved if the source 16 and detector 20 are located generally 20 mm from the front edge of their respective slots, and if the first collimator 24 has a slot of length generally 30 mm. Similarly, the second collimator 26 comprises lead shielding having similarly oriented slots to receive radiation 30 (FIG. 3) backscattered by the refractory material through the metal wall 6.

First adjustment means in the form of a first adjustment device 32 enables the separation between the first 24 and second 26 collimators to be adjusted, thereby enabling the separation between the source 16 and the detector 20 to be adjusted. Second adjustment means in the form of a second adjustment device 34, for enabling the source recess (i.e. the distance of the source 16 from front edge 36 of first collimator 24) to be adjusted, and a third adjustment device 38, for enabling the detector recess (i.e. the distance of the detector 20 from front edge 40 of second collimator 26) to be adjusted, enables adjustment of the distance of the source 16 and the detector 20 from the wall 6, the distance of the front face of the first 24 and second 26 collimators from the wall 6 typically being about 10 mm.

Attraction means in the form of two sets of magnetic wheels 42, 44 and a permanent magnet 46 arranged on the body generate magnetic attractive forces to maintain the magnetic wheels 42, 44 in contact with the wall 6 of the unit 8 to maintain a fixed distance of the source 16 and detector 20 from the wall 6 as the body 10 is suspended via a cable 48 (FIG. 1) attached to lifting eye bolt 14 and passing over a pulley 50 and the body 10 to be lowered by means of a winch 52 to scan the external surface of the wall 6.

Figure 3:
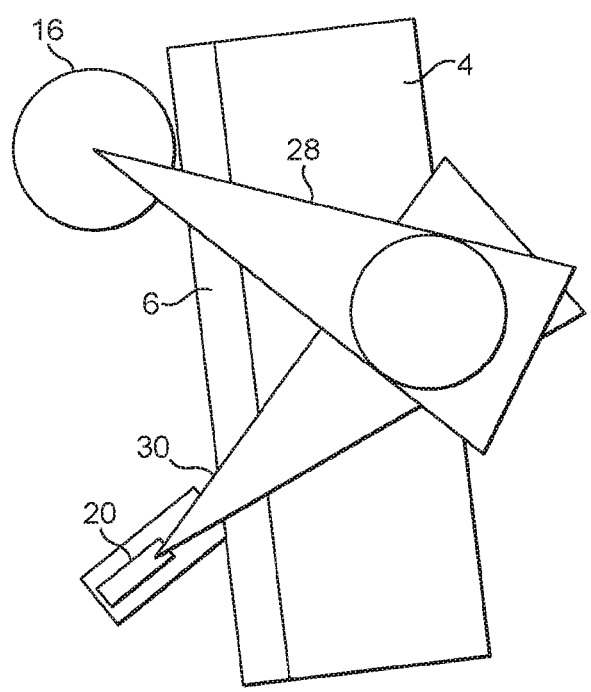
FIG. 3 is a schematic view of back-scattering of gamma rays from a region of refractory material in the arrangement of FIG. 1.
Figure 4:
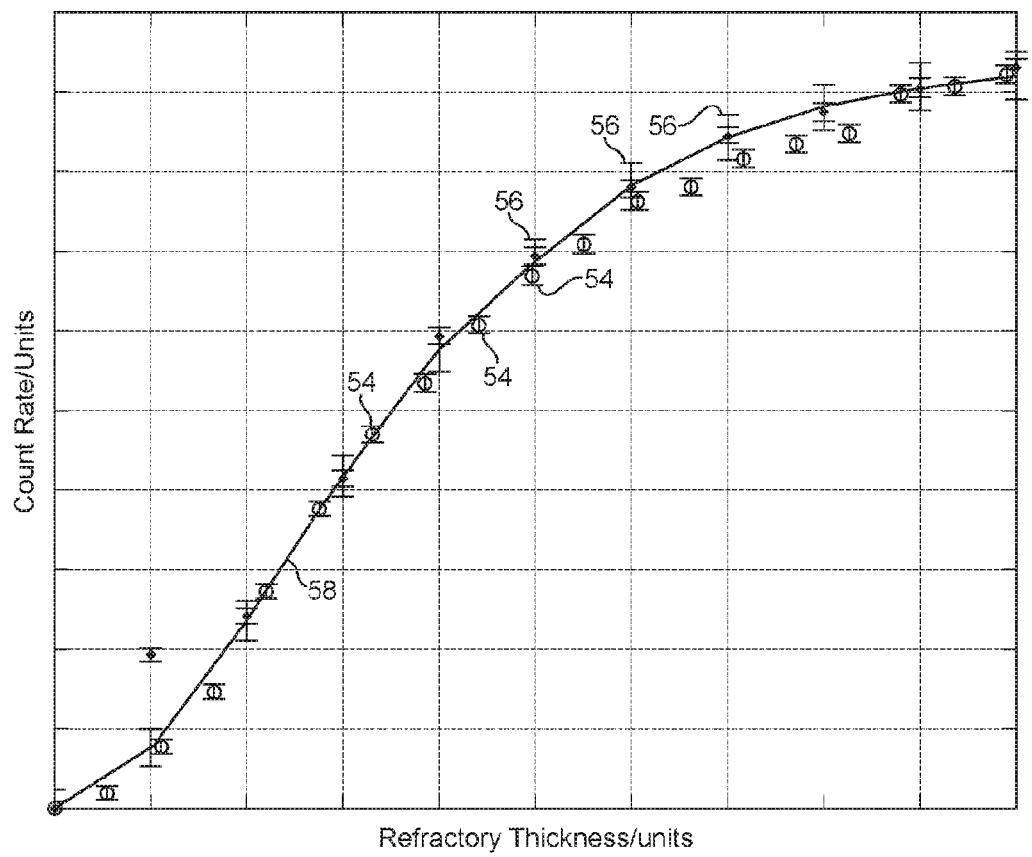
FIG. 4 shows a comparison between predicted and measured variation of measured counter rates with thickness of refractory material in the apparatus of FIG. 1.

As shown in greater detail in FIG. 3, the source 16 emits a divergent beam 28 of gamma radiation through the steel vessel wall 6 and the refractory material 4, and the refractory material 4 back-scatters a portion 30 of the incident gamma radiation to the detector 20. The variation of count rate of detector 20 (and therefore output signal of converter 22) with thickness of refractory material 4 is shown in FIG. 4. FIG. 4 shows first data points 54 corresponding to a first refractory sample, second data points 56 corresponding to a second refractory sample, and a continuous curve 58 showing the results of a Monte Carlo simulation, from which it can be seen that there is good agreement between the predicted and measured behavior of the apparatus 2.

Referring to FIG. 5, the results of a Monte Carlo simulation to determine variation of detector count rate with source recess and source/detector separation is shown, which enables the apparatus 2 to be adjusted for optimum responsiveness. A two parameter study was conducted to determine the best separation of the first 24 and second 26 collimators for the apparatus 2. The two parameters were source recess and collimator position. The recess is the distance of the source 16 from the front edge 36 of the first collimator 24. The collimator position is the amount of space between the two collimators 24, 26, and is ultimately a measure of source 16 and detector 20 position. The two parameters were varied and two Monte-Carlo simulations were conducted for each parameter combination. The first was a simulation with 75 mm of refractory and the second with 100 mm, as a result of which the simulation predicted a count rate. Using standard Poisson statistics it was possible to determine the minimum amount of time required to be confident in the fractional change in the measurements between 75 and 100 mm of refractory thickness, a good apparatus 2 being one that has the minimum value for this time. Plotted is 1/time and the maximum value was sought for this metric. This enabled the parameters to be adjusted so that the apparatus 2 operated in its optimum region 60.

Referring to FIG. 6, the results of a Monte Carlo simulation of the effect of wall 6 thickness on count rate is shown. For a wall 6 thickness of 19 mm, region 63 bounded by curves 62 and 64 is given, the curves 62 and 64 corresponding respectively to high and low density refractory materials 4. Similarly, for a wall 6 thickness of 25 mm, region 67 bounded by curves 66 and 68 is given, the curves 66 and 68 corresponding respectively to high and low density refractory materials 4.

Referring to FIG. 7, an apparatus 102 for measuring thickness of refractory material lining a metal wall of a vessel such as a steel walled fluid catalytic cracking unit has a body 110 having transport wheels 112 adjacent one end thereof.

Radiation emitting means in the form of a 740 MBeq Cs-137 source 116 of gamma radiation is arranged adjacent one face 118 of the body 110 and radiation detecting means in the form of a 50 mm cylindrical sodium iodide crystal gamma radiation detector 120 is arranged on the same face 118 of the body 110 so that the crystal axis of the detector 120 can be arranged generally parallel to the wall of the unit.

The detector 120 is connected to output means for outputting a signal representing the number of counts by the detector 120.

Shielding means in the form of a first collimator 124 around the source 116 and a second collimator 126 around the detector 120 minimise the number of gamma photons passing directly from the source 116 to the detector 120. The first collimator 124 comprises lead shielding having slots generally in the plane of FIG. 7 to cause a beam of radiation to be directed through the wall and into the refractory material. It is found that particularly advantageous results are achieved if the source 116 and detector 120 are located generally 20 mm from the front edge of their respective slots, and if the first collimator 124 has a slot of length generally 30 mm. Similarly, the second collimator 126 comprises lead shielding having similarly oriented slots to receive radiation backscattered by the refractory material through the metal wall.

Attraction means in the form of two sets of magnetic wheels 142, 144 and a permanent magnet 146 arranged on the body 110 generate magnetic attractive forces to maintain the magnetic wheels 142, 144 in contact with the wall of the unit to maintain a fixed distance of the source 116 and detector 120 from the wall as the body 110 is suspended via a cable to be lowered by means of a winch to scan the external surface of the wall.

Air extraction means in the form of a fan 170 is provided at the back of the apparatus 102. Fan 170 is connected by ducting 171 to an air gap 172 between the detector 120 and collimator 126, on one side, and the face of apparatus 102 that is placed against the wall to be scanned, on the other. Air supply means, in the form of fan 173 is also provided on the back of apparatus 102. In use, air fan 173 draws ambient air from the surroundings and urges it (as generally indicated by arrow A) toward the entrance 174 of the air gap 172. An excess of air is supplied and that excess is vented through the sides and end of apparatus 102 (as generally indicated by arrow B). Fan 170 draws air out of the air gap 172 and vents it to the surroundings (as generally indicated by arrow C). As a result, air is drawn in through the entrance 174 into the air gap 172 (as generally indicated by arrow D). Thus a curtain of relatively cool air close to the ambient temperature is continuously passed across the face of the collimator 126 and forms a barrier to heat transfer from the hot wall being scanned, and provides for removal of heat from the region before that heat can reach the detector 120. In some embodiments the supply of air D to the air gap 172 may flow past detector 120 and through an opening in collimator 126 into a central region of the air gap 172. The air flow may then exit the air gap 172 via both the ducting 171 and the 'entrance' 174, before being exhausted from the apparatus as generally indicated by arrows C and B.

It will be appreciated by persons skilled in the art that the above embodiment has been described by way of example only and not in any limitative sense, and that various alterations and modifications are possible without departure from the scope of the invention as defined by the appended claims. For example, although the invention has been described in relation to determining the thickness of a refractory material lining a vessel, the invention could also be used to determine the thickness of carbon deposits such as coke on the refractory material.

The invention claimed is:

1. An apparatus for determining thickness of refractory material lining a metal vessel, the apparatus comprising:
   a source of gamma radiation for emitting gamma radiation through a metal wall of the vessel and into said lining material, wherein some of said gamma radiation is scattered by said lining material;
   a radiation detector for detecting said gamma radiation scattered by said lining material through the wall of the vessel;
   a shield for attenuating radiation transmitted directly from said source of gamma radiation to said radiation detector, wherein the shield comprises a collimator member of radiation attenuating material having at least one slot for accommodating said source of gamma radiation; and
   a converter for providing at least one output signal dependent on the quantity of radiation scattered by said lining material through the wall of the vessel and detected by said radiation detector.

2. The apparatus according to claim 1, wherein the radiation detector comprises at least one scintillation crystal and at least one photomultiplier.

3. The apparatus according to claim 1, further comprising a first adjustor for adjusting a distance between the source of gamma radiation and the radiation detector.

4. The apparatus according to claim 1, further comprising a second adjustor for adjusting a distance of the source of gamma radiation and/or radiation detector from the wall of the vessel.

5. The apparatus according to claim 1, wherein said source of gamma radiation is arranged between 5 mm and 40 mm from an edge of said slot in a first direction.

6. The apparatus according to claim 1, wherein at least one said slot extends 10 mm to 50 mm from said source of gamma radiation in a second direction.

7. An apparatus for determining thickness of refractory material lining a metal vessel, the apparatus comprising:
   a source of gamma radiation for emitting gamma radiation through a metal wall of the vessel and into said lining material, wherein some of said gamma radiation is scattered by said lining material;
   a radiation detector for detecting said gamma radiation scattered by said lining material through the wall of the vessel;
   a converter for providing at least one output signal dependent on the quantity of radiation scattered by said lining material through the wall of the vessel and detected by said radiation detector; and
   at least one magnet for maintaining the source of gamma radiation and/or radiation detector within a predetermined distance of the wall of the vessel.

8. The apparatus according to claim 7, wherein the at least one magnet comprises at least one magnetic wheel adapted to engage a wall of the vessel.

9. An apparatus for determining thickness of refractory material lining a metal vessel, the apparatus comprising:
   a source of gamma radiation for emitting gamma radiation through a metal wall of the vessel and into said lining material, wherein some of said gamma radiation is scattered by said lining material;
   a radiation detector for detecting said gamma radiation scattered by said lining material through the wall of the vessel;
   a converter for providing at least one output signal dependent on the quantity of radiation scattered by said lining material through the wall of the vessel and detected by said radiation detector; and
   at least one winch apparatus for enabling the apparatus to scan a surface of the vessel assisted by gravity.

10. An apparatus for determining thickness of refractory material lining a metal vessel, the apparatus comprising:

a source of gamma radiation for emitting gamma radiation through a metal wall of the vessel and into said lining material, wherein some of said gamma radiation is scattered by said lining material;

a radiation detector for detecting said gamma radiation scattered by said lining material through the wall of the vessel;

a converter for providing at least one output signal dependent on the quantity of radiation scattered by said lining material through the wall of the vessel and detected by said radiation detector;

an air gap located such that, during operation of the apparatus, the air gap is between the detector and a surface of an object being scanned; and an air extractor operable to vent air from the air gap out of the apparatus.

11. The apparatus according to claim 10, wherein the apparatus comprises ducting linking the air extractor to the air gap.

12. An apparatus for determining thickness of refractory material lining a metal vessel, the apparatus comprising:

a source of gamma radiation for emitting gamma radiation through a metal wall of the vessel and into said lining material, wherein some of said gamma radiation is scattered by said lining material;

a radiation detector for detecting said gamma radiation scattered by said lining material through the wall of the vessel;

a converter for providing at least one output signal dependent on the quantity of radiation scattered by said lining material through the wall of the vessel and detected by said radiation detector;

an air gap located such that, during operation of the apparatus, the air gap is between the detector and a surface of an object being scanned; and an air supplier configured to draw ambient air from the apparatus' surroundings and urge the ambient air towards the air gap.

13. A method of determining thickness of lining material lining a metal vessel, the method comprising:

emitting gamma radiation from a gamma radiation source through a metal wall of the vessel and into said lining material, wherein some of said gamma radiation is scattered by said lining material;

detecting, using a radiation detector, gamma radiation scattered by said lining material through the wall of the vessel;

withdrawing air from an air gap located between the radiation detector and the wall of the vessel; and providing at least one output signal dependent on the quantity of gamma radiation detected.

14. The method according to claim 13, wherein the method comprises maintaining an air curtain between the radiation detector and the wall of the vessel.

15. The method according to claim 13, wherein the method comprises urging air toward an entrance of the air gap using an air supplier.

16. The method according to claim 15, wherein a greater volume of air is urged toward the air gap by the air supplier than is withdrawn from the air gap.

* * * * *